US006224593B1

United States Patent
Ryan et al.

(10) Patent No.: US 6,224,593 B1
(45) Date of Patent: May 1, 2001

(54) TISSUE SEALING USING MICROWAVES

(75) Inventors: Thomas Patrick Ryan, Fort Collins, CO (US); B. Stuart Trembly, Hanover, NH (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/229,850

(22) Filed: Jan. 13, 1999

(51) Int. Cl.[7] .................................................. A61B 18/18
(52) U.S. Cl. .............................. 606/41; 606/33; 606/213; 606/49; 607/101
(58) Field of Search ................................ 606/41–52, 232, 606/213, 33; 607/89–92, 100–101; 128/303.1

(56) References Cited

U.S. PATENT DOCUMENTS

| | | | |
|---|---|---|---|
| 4,266,547 | * | 5/1981 | Komiya .............................. 128/303.1 |
| 4,763,671 | | 8/1988 | Goffinet . |
| 4,776,334 | | 10/1988 | Prionas . |
| 5,150,717 | | 9/1992 | Rosen et al. . |
| 5,258,006 | | 11/1993 | Rydell et al. . |
| 5,269,780 | | 12/1993 | Roos . |
| 5,376,087 | | 12/1994 | Haber et al. . |
| 5,458,598 | * | 10/1995 | Feinberg et al. ........................ 606/52 |
| 5,470,309 | | 11/1995 | Edwards et al. . |
| 5,472,441 | | 12/1995 | Edwards et al. . |
| 5,507,743 | | 4/1996 | Edwards et al. . |
| 5,507,744 | * | 4/1996 | Tay et al. ............................... 606/50 |
| 5,542,945 | * | 8/1996 | Fritzsch .................................. 606/48 |
| 5,735,848 | * | 4/1998 | Yates et al. ............................. 606/48 |
| 5,766,167 | * | 6/1998 | Eggers et al. .......................... 606/46 |
| 5,792,139 | * | 8/1998 | Chambers et al. ..................... 606/41 |
| 5,810,810 | * | 9/1998 | Tay et al. ............................... 606/50 |
| 5,951,552 | * | 9/1999 | Long et al. ............................. 606/46 |
| 6,035,238 | * | 3/2000 | Ingle et al. ............................. 607/89 |

* cited by examiner

*Primary Examiner*—John P. Leubecker
*Assistant Examiner*—Ahmed Farah

(57) ABSTRACT

A method and apparatus for thermal treatment of tissue employing microwave energy is disclosed. Preferably, the apparatus includes an elongated member having a tissue capturing portion. A microwave conductor operatively mounts with the elongated member and has a forward conductor end. The microwave conductor is adapted for movement between an unadvanced position where the forward conductor end is displaced from the tissue capturing portion and an advanced position where the forward conductor end is adjacent to the tissue capturing portion to direct microwave energy toward the body tissue portion supported therein. A source of microwave energy in electrical communication with the microwave conductor supplies microwave energy having a frequency ranging from about 400 MHz to about 2500 MHz. Preferably, the microwave conductor includes an active conductor and a return conductor in a coaxial arrangement. The forward conductor end may be uninsulated or insulated. Most preferably, a handle is connected to the elongated member.

19 Claims, 7 Drawing Sheets

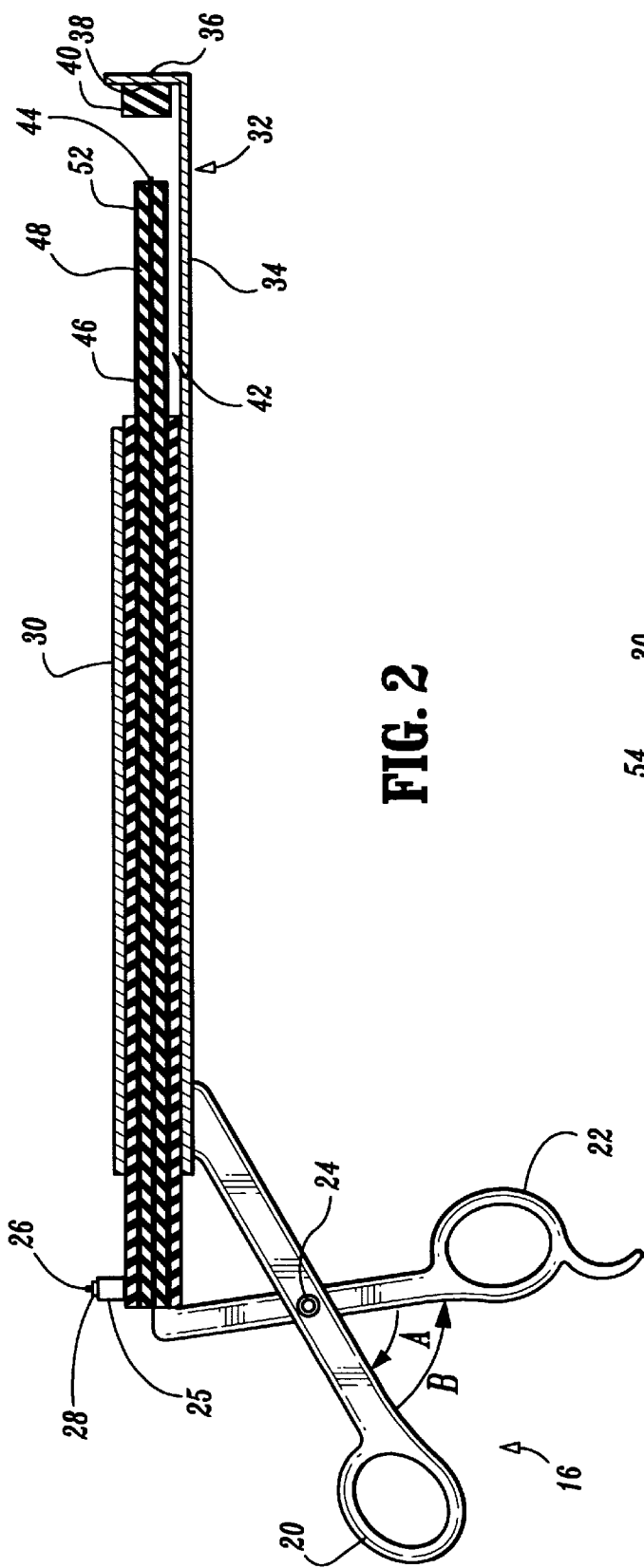
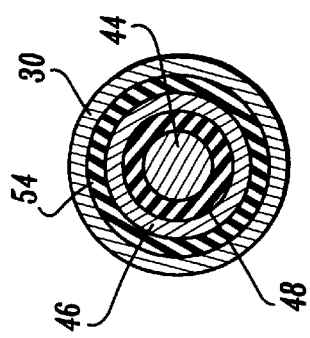
FIG. 2
FIG. 3

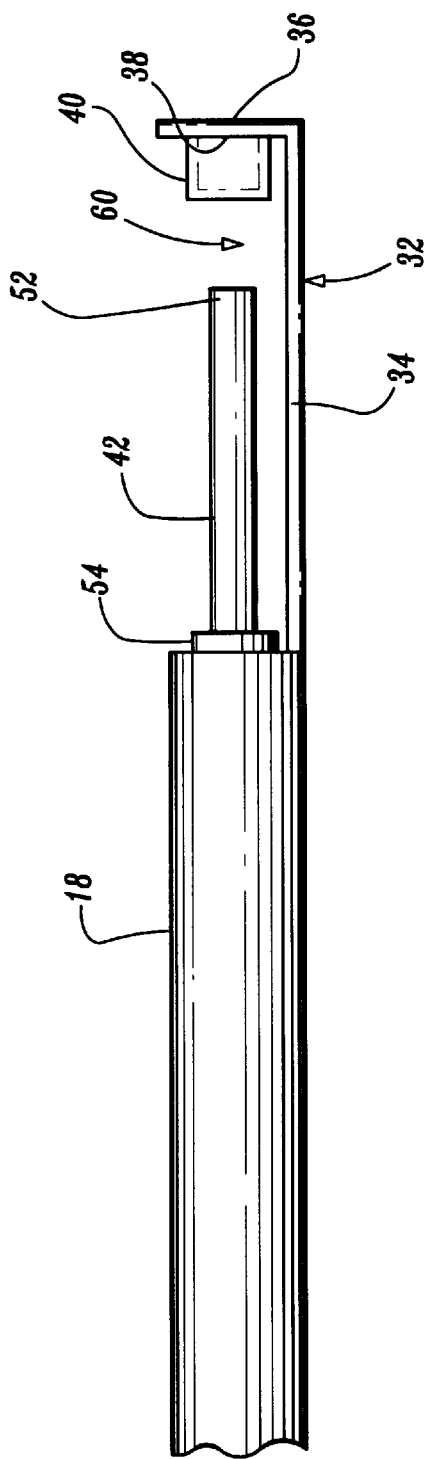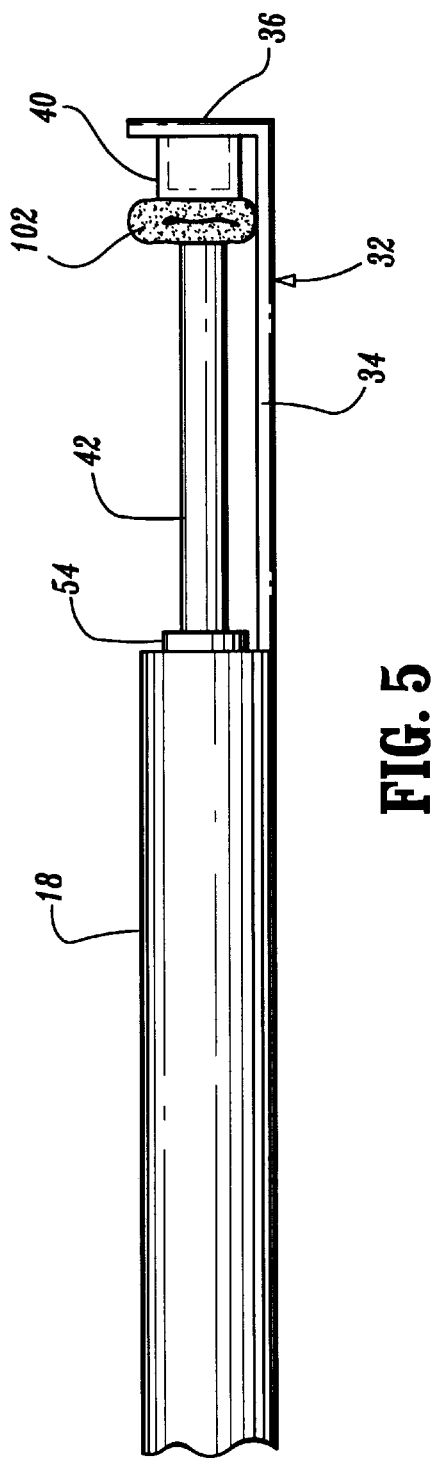

TISSUE SEALING USING MICROWAVES

1. TECHNICAL FIELD

The present disclosure relates generally to apparatus and methods for thermally treating tissue and more particularly, to an apparatus for applying microwave frequency energy to seal a body vessel or tissue.

2. BACKGROUND OF THE DISCLOSURE

In many surgical procedures, body vessels, e.g., blood vessels, ducts, adhesions, fallopian tubes, etc. . . . are sealed to defunctionalize or close the vessel. Traditionally, staples, clips or sutures have been used to close a body vessel. However, these traditional procedures often leave foreign body material inside a patient. In an effort to reduce foreign body material left within the patient and to more effectively seal the body vessel, energy techniques that seal by heat processes have been employed. The present disclosure include apparatus and methods that combine applying a force to greatly compress the target tissue as well as applying energy such that collagen will melt and reform in a permanently compressed state.

Current vessel sealing procedures utilize heat treatment in the form of radio frequency (RF) energy in the frequency range of 200 to 1000 kHz to heat and desiccate tissue causing closure and sealing of the body vessel. For example, U.S. Pat. No. 5,258,006 discloses electrosurgical bipolar RF forceps which cauterize blood vessels during a percutaneous laparoscopic cholecystectomy procedure.

Accordingly, there is a need for an apparatus which provides a uniform, controllable seal and that is capable of providing such a seal with minimum collateral damage to body tissue.

SUMMARY

Accordingly, the present disclosure is directed to apparatus for thermal treatment of tissue. The apparatus has particular application in sealing of body tissue, including vessels such as blood vessels, fallopian tubes, bundled tissue incl. vein, artery and/or nerves, ducts, adhesions, etc. The apparatus advantageously compresses the tissue and provides a non-stick application of microwave frequency electrosurgical energy thereby avoiding sticking of tissue to the apparatus and providing a more controllable seal. The apparatus can also seal body tissue without undesired collateral damage. It is contemplated that at least a portion of the apparatus may be constructed from flexible material. It is further contemplated that at least a portion of the apparatus may be constructed from a deformable material.

The apparatus includes an elongated member having proximal and distal ends and having a tissue capturing portion for capturing tissue. The apparatus further includes a microwave conductor operatively mounted with the elongated member and having a forward conductor end. The microwave conductor is adapted for reciprocal axial movement relative to the elongated member between an unadvanced position where the forward conductor end is displaced from the tissue capturing portion and an advanced position where the forward conductor end is adjacent to the tissue capturing portion to direct microwave energy toward the body tissue portion supported therein. A source of microwave energy in electrical communication with the microwave conductor supplies microwave energy having a frequency ranging from about 400 MHz to about 2500 MHz.

In a preferred embodiment, the microwave conductor includes an active or inner conductor and a return or outer conductor mounted in coaxial arrangement. The forward conductor end of the microwave conductor is uninsulated to expose the active conductor and the return conductor to permit direct contact with the body tissue portion. Preferably, the tissue capturing portion defines a tissue capturing surface whereby the tissue capturing surface comprises a dielectric material. It is also envisioned that an insulator can be mounted to the forward conductor end to prevent direct contact between the body tissue and the forward conductor end to limit collateral tissue damage and inhibit eschar buildup and sticking to the apparatus.

In one preferred embodiment, the active conductor of the microwave conductor is dimensioned to extend distally beyond the return conductor. Desirably, an insulating material is disposed about a portion of the active conductor extending distally beyond the return conductor.

In another preferred embodiment, the microwave conductor includes at least one ground plane in electrical contact with the outer conductor. Preferably, an insulating material is disposed on a tissue contacting surface of the one ground plane.

In yet another preferred embodiment, the return conductor of the microwave conductor is dimensioned to extend distally beyond the active conductor.

In a most preferred embodiment, the apparatus includes a handle connected to the elongated member. The handle includes a manual actuator operatively connected to the microwave conductor. The actuator is movable to cause corresponding movement of the microwave conductor between the unadvanced and the advanced positions.

A method is disclosed for sealing body tissue and including the steps of: positioning a surgical instrument adjacent body tissue; and supplying microwave energy having a frequency ranging from about 400 MHz to about 2500 MHz to the surgical instrument to cause desiccation of the body tissue portion to thereby substantially seal a portion of the body tissue.

In a preferred embodiment, the surgical instrument includes a microwave conductor, and the step of positioning includes placing the microwave conductor in direct contact with the body tissue. Preferably, the surgical instrument includes an elongated member having a tissue capturing portion at a distal end, and the step of positioning includes arranging the surgical instrument such that the body vessel portion is disposed between the microwave conductor and the tissue capturing portion. Most preferably, the step of positioning includes clamping the body vessel portion between the microwave conductor and the tissue capturing portion. Desirably, the microwave conductor includes an active conductor and a return conductor mounted in coaxial arrangement, the forward conductor end of the microwave conductor being uninsulated to expose the active conductor and the return conductor, and wherein the step of positioning includes directly contacting the vessel portion with the forward conductor end.

BRIEF DESCRIPTION OF THE DRAWINGS

Preferred embodiments of the disclosure are described herein with reference to the drawings wherein:

FIG. 2 is a side view in partial cross-section, of the microwave instrument of FIG. 1 illustrating the elongated portion connected to the handle and the microwave conductor mounted within the elongated portion;

FIG. 3 is a transverse cross-sectional view of the microwave instrument taken along lines 3—3 of FIG. 1;

FIG. 4 is an enlarged side view of the distal end of the microwave instrument of FIG. 1 illustrating the microwave conductor in an initial unadvanced position;

FIG. 5 is a view similar to the view of FIG. 4 illustrating the microwave conductor in an advanced position to treat a vessel portion;

DETAILED DESCRIPTION OF THE INVENTION

The preferred embodiment(s) of the methods and apparatus disclosed herein are discussed in terms of tissue sealing procedures and instrumentation. It is contemplated that the present methods and apparatus find application in both open and minimally invasive procedures including endoscopic and laparoscopic procedures wherein access to the surgical site is achieved through a cannula, small incision, or naturally occurring orifice.

In the discussion which follows, the term "proximal", as is traditional, will refer to the portion of the structure which is closer to the operator, while the term "distal" will refer to the portion which is further from the operator.

Figure 1:
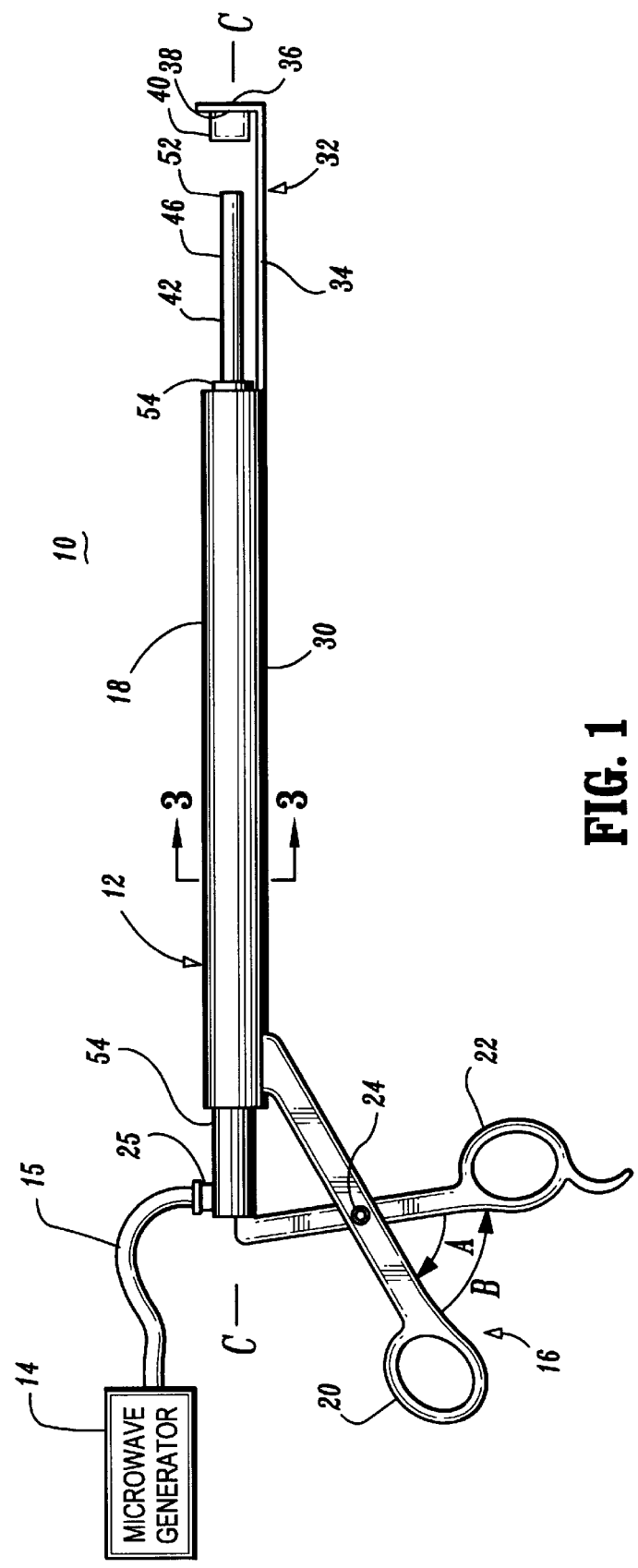
FIG. 1 is a side view of a microwave system in accordance with the principles of the present disclosure including a microwave instrument and a microwave generator.

In accordance with the present disclosure, referring now in detail to the drawings wherein like reference numerals identify similar or like components throughout the several views, FIG. 1 illustrates a side view of a microwave system 10 in accordance with the principals of the present disclosure. System 10 includes a microwave instrument 12 and a microwave generator 14 electrically connected to instrument 12 by coaxial cable 15. Generator 14 provides microwave frequency energy for application to tissue. Generator 14 may be any commercially available generator suitable for delivering microwave energy and includes an amplifier, such as model 100 S1G4 manufactured by Amplifier Research, Souderton, Pa., USA. The driving signal is provided by a synthesizer such as HP 83731 B manufactured by Hewlett-Packard, Palo Alto, Calif., USA. Generator 14 preferably supplies microwave energy having a frequency ranging from about 400 MHz to about 2500 MHz.

Instrument 12 includes a handle 16 and an elongated member or chassis 18 extending distally from handle 16. Handle 16 includes first and second handle grips 20, 22 pivotally connected to each other about pivot pin 24. Each handle grip 20, 22 defines a finger loop. First handle grip 20 is fixedly connected to elongated member 18 by suitable means including screws, adhesives or the like. Second handle grip 22 pivots about pivot pin 24 movable relative to first handle grip 20 to retract and advance distally mounted end effectors (described in greater detail below) for microwave communication and achieving an adequate compression force for sealing tissue. As shown in FIG. 2, handle 16 also includes a coaxial connector 25 having a microwave inner conductor terminal 26 and a microwave outer conductor terminal 28 for connecting instrument 12 to a source of microwave frequency energy, namely, microwave generator 14 (FIG. 1).

Figure 6:
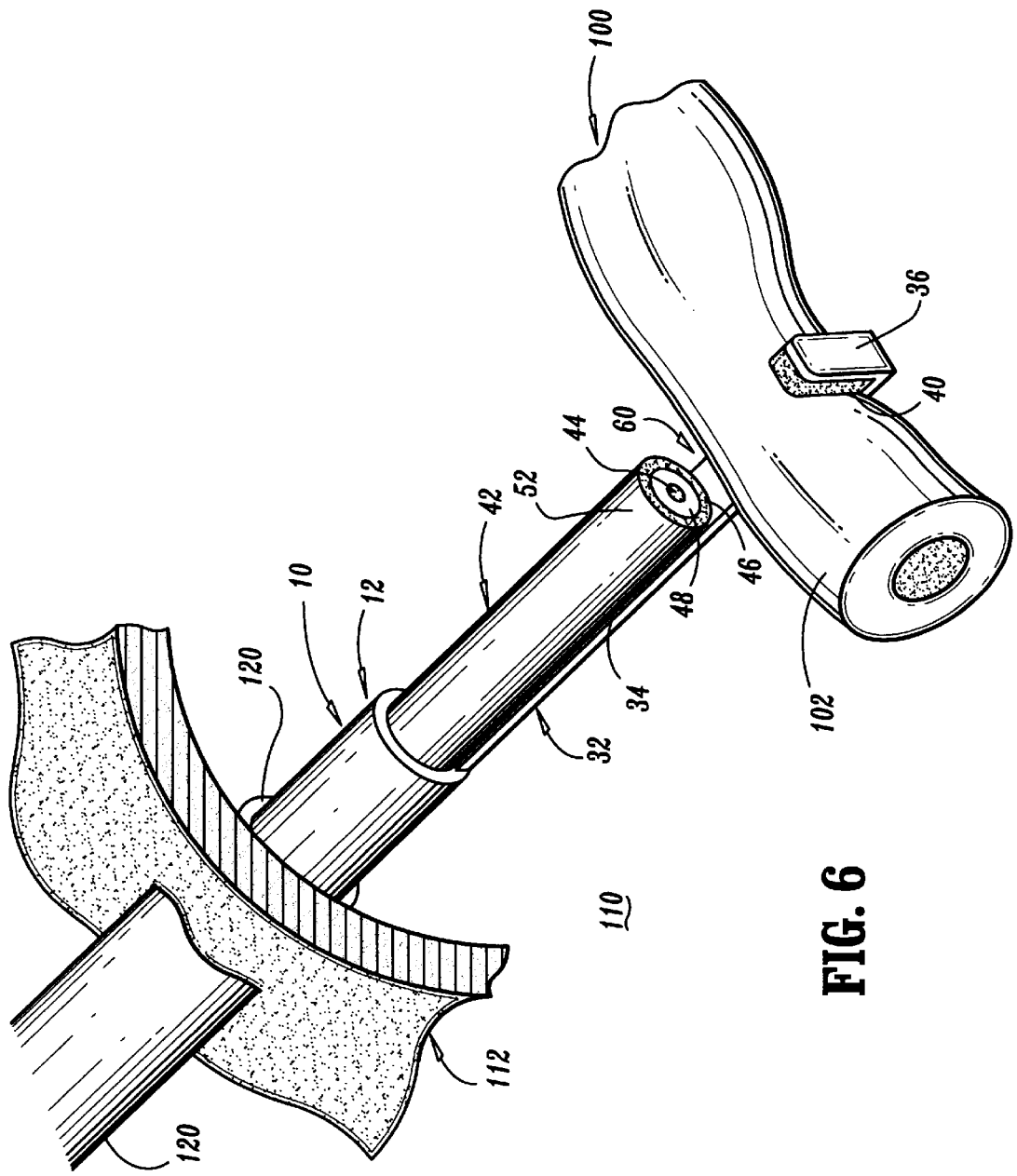
FIG. 6 is an enlarged perspective view of a vessel treated within the microwave system.

Elongated member or chassis 18 of instrument 12 includes outer tube 30 and a chassis extension 32 extending from the distal end of outer tube 30. Outer tube 30 defines a longitudinal opening therethrough, preferably, having a diameter ranging from 5–10 millimeters for insertion through a trocar 120 (FIG. 6). It is contemplated that outer tube 30 may be constructed of various sizes according to the particular surgical application.

Chassis extension 32 is, preferably, monolithically formed with outer tube 30. Alternatively, outer tube 30 may be brazed, welded or soldered to the chassis extension 32. Chassis extension 32 defines a longitudinal portion 34 and a tissue capturing portion 36 disposed adjacent the distal end of longitudinal portion 34. Tissue capturing portion 36 extends in general transverse relation to longitudinal portion 34 and axis C—C, and defines a capturing surface 38 dimensioned to capture tissue positioned thereagainst during operation of instrument 12. Tissue capturing portion 36, preferably, has a layer of dielectric material 40 disposed on capturing surface 38 to electrically insulate chassis extension 32 and outer tube 30 from the microwave circuit.

With reference to FIGS. 1–3, instrument 12 further includes a microwave conductor 42 extending through outer tube 30 and is axially movable therewithin. As best shown in FIGS. 2 and 3, microwave conductor 42 includes a conventional coaxial microwave transmission cable having an inner active conductor 44 and an outer return conductor 46 separated by a layer of insulation 48 and surrounded by an outer insulating sheath 54. Conductor 42 is mechanically connected to second handle grip 22 whereby pivotal movement of handle grip 22 (shown by arrows A and B in FIGS. 1 and 2) causes corresponding reciprocal axial movement of conductor 42 (along axis C—C) between an unadvanced position (FIG. 4) and an advanced position (FIG. 5). More particularly, pivotal movement of second handle grip 22 towards first handle grip 20 (in the direction of arrow A in FIG. 1) effects distal axial movement of conductor 42 while pivotal movement of second handle grip 22 away from handle grip 20 (in the direction of arrow B) effects proximal movement of conductor 42. Further, conductor 42 is manipulated axially, in the embodiment shown in FIGS. 1–6, to achieve a sufficient compressive force for sealing tissue.

In one preferred embodiment, distal end 52 of conductor 42 is uninsulated or exposed to directly contact tissue supported by tissue capturing portion 36 of chassis extension 32. Such exposure may alter the transmission energy field at least adjacent distal end 52 of conductor 42, the benefits of such configuration being discussed hereinbelow.

The use of system 10 in conjunction with sealing a body vessel, e.g., a blood vessel 100, will now be described. Initially, the surgical site is accessed through conventional techniques. With reference to FIG. 6, during laparoscopic procedures, a body cavity 110 may be insufflated with insufflation gases to raise a body cavity wall 11 2 from the internal organs (not shown). A trocar 120 may be utilized to enter a body cavity wall 112 to provide access to the operative site. Instrument 12 is manipulated to the operative site such that a targeted vessel portion 102 is positioned within the recess or gap 60 defined between distal end 52 of conductor 42 and tissue capturing portion 36 of chassis extension 32. It is envisioned that instrument 12 may be constructed from flexible materials such as suitable alloys and rubbers and resins including plasticizers, for providing additional degrees of freedom and positioning capabilities. It is further envisioned that instrument 12 may be constructed from a deformable material such as suitable alloys and polymers, providing additional orientations and predetermined configurations for positioning instrument 12.

With vessel 100 appropriately positioned, second handle grip 22 (FIG. 1) is pivoted in the direction of arrow A to cause advancement of conductor 42 to compress vessel portion 102 between conductor 42 and tissue capturing portion 36, as best shown in FIG. 5.

Referring back now to FIG. 6, microwave generator 14 (FIG. 1) is actuated to provide microwave energy to instrument 12. Due to the exposure of distal end 52 of conductor 42, microwave frequency current flows from inner active conductor 44, through vessel 100, and subsequently through outer return conductor 46. More particularly, the low resistive characteristics of the tissue in direct contact with distal end 52 of conductor 42 provides a lower impedance path for the microwave energy thereby inducing the current path or flow through vessel portion 102 to cause a circular zone of desiccation within vessel portion 102. As discussed above, the tissue targeted for treatment, as here, vessel portion 102, is compressed for sealing in addition to the application of microwave energy to the tissue. Handle grips 20 and 22 are manipulated to produce a compressive force in an amount sufficient to adequately compress the captured tissue. Preferably, such force is in a range of about 500–400 gms. Accordingly, vessel portion 102 becomes sealed as desired.

Figure 6A:
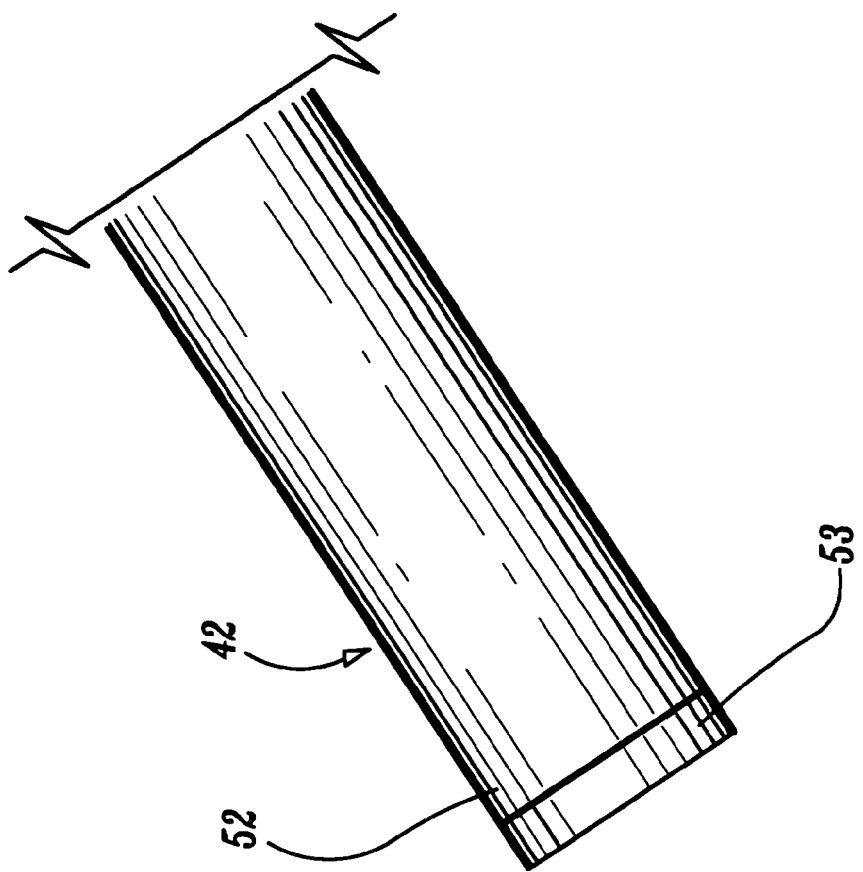
FIG. 6A is a side view of an alternate embodiment of the microwave conductor showing an insulating dielectric material on the distal end.

In another preferred embodiment, as best shown in FIG. 6A, a dielectric portion 53 is fixedly mounted to distal end 52 of microwave conductor 42. In this embodiment, direct contact between microwave conductor 42 and tissue targeted for treatment is not required enabling a surgeon to treat tissue in particular surgical applications where contacting tissue is not desirable, providing instrument 12 a broader range of utility for the surgeon. It is envisioned that dielectric portion 53 may be removably mounted to distal end 52 of microwave conductor 42 and may be constructed from any suitable dielectric material. Dielectric portion 53 may also prevent buildup of residue, eschar and the like on microwave conductor 42, facilitating prolonged use of instrument 12 before cleaning is required. In use, conductor 42 irradiates microwave frequency energy through insulator 53 to treat body tissue. Distal end 52 of conductor 42 does not directly contact the tissue targeted for treatment. However, manipulation of handle grips 20, 22 forces insulator 53 to compress tissue, as discussed, to sufficiently seal the tissue portion when microwave energy is applied.

The application of microwave frequency energy inhibits sticking of instrument 12 to vessel 100. In addition, the microwave energy provides a more controllable seal in that as the tissue desiccates, the electrical properties change so as to absorb less of the applied energy. It is envisioned that instrument 12 may also be utilized in surgical applications, whereby a body vessel requires sealing but collateral damage to the vessel is to be avoided, such as treating fibrous connective tissue. For example, in the treatment of tendons and the like, instrument 12 irradiates the tissue to temperatures in the range of 65° C.–80° C. to shrink collagen in the tendon reducing its thickness 25%–50%. Higher irradiating temperatures are also contemplated.

Figure 7:
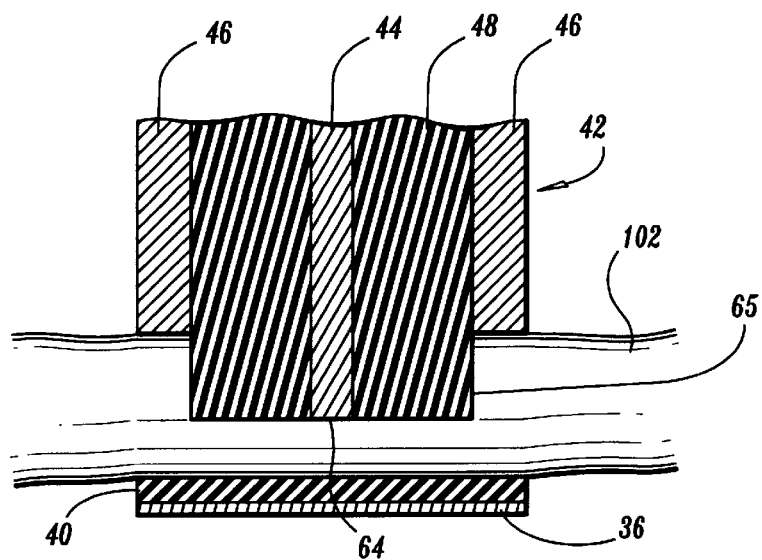
FIG. 7 is a cross-sectional view, in part elevation, of an alternate embodiment of the microwave instrument.

Referring now to FIG. 7, there is illustrated one particular embodiment of inner active conductor 44 and outer return conductor 46 of instrument 12 (shown in FIGS. 1–6). In this embodiment, inner active conductor 44 of conductor 42 has a forward portion 64 which extends to protrude beyond outer return conductor 46. A dielectric material 65, e.g., PTFE, surrounds the distal end of inner active conductor 44. This configuration provides a microwave energy path that travels from inner active conductor 44 through a compressed vessel 102 to reach outer return conductor 46. Thus, the desiccation zone is broadened, in effect, the electromagnetic wave launched from inner active conductor 44 will travel a broader path to outer return conductor 46.

Figure 8:
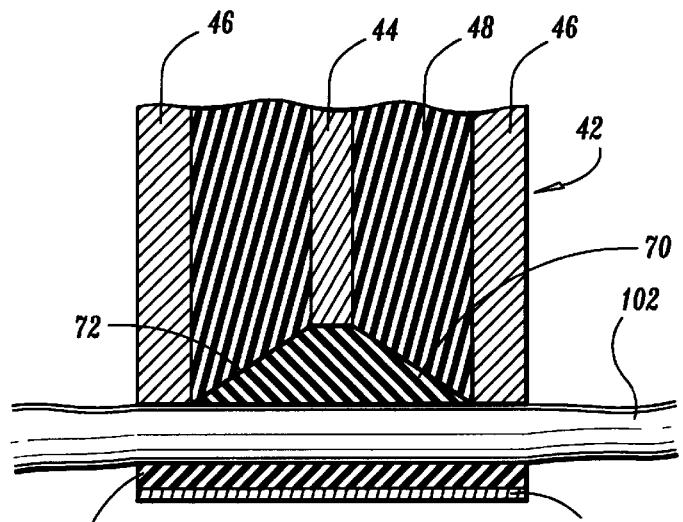
FIG. 8 is a cross-sectional view, in part elevation, of another alternate embodiment of the microwave instrument.

FIG. 8 illustrates an alternate embodiment where outer return conductor 46 extends beyond active inner conductor 44. This configuration defines a recess 70 in the shape of a truncated cone. Dielectric portion 72 is disposed within recess 70. This configuration spreads the desiccation zone of vessel 102 by broadening the current distribution as the current travels from inner active conductor 44 to outer return conductor 46. The electromagnetic wave launched from inner active conductor 44 will broaden through dielectric portion 72 before contacting vessel 102.

Figure 9:
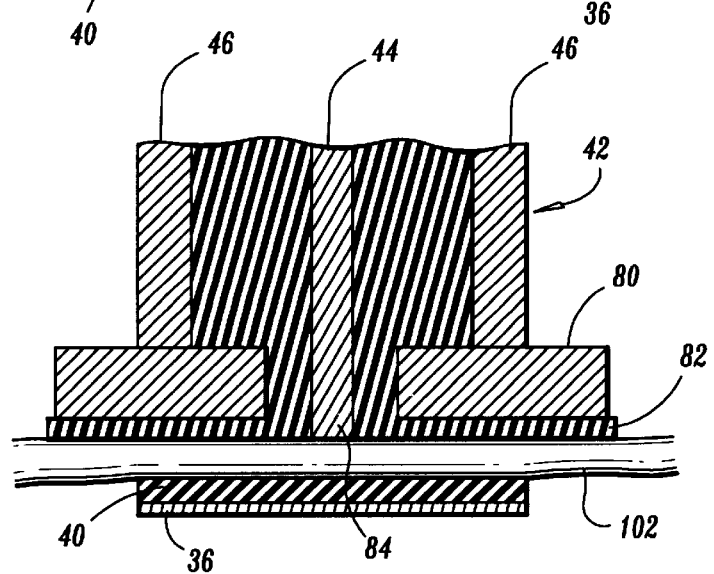
FIG. 9 is a cross-sectional view, in part elevation, of another alternate embodiment of the microwave instrument.

FIG. 9 illustrates another embodiment where outer return conductor 46 includes ground planes 80. Inner active conductor 44 protrudes beyond ground planes 80 contacting vessel portion 102. Dielectric portion 82 is disposed on ground planes 80. Distal end 84 of inner active conductor 44 may be positioned in flush cooperation with dielectric portion 82 or extend beyond the contact region of vessel portion 102. This alternate configuration will broaden the cross-sectional area of vessel 102 that is affected by the electromagnetic wave launched from inner active conductor 44. Current will travel through vessel portion 102 from inner active conductor 44, to ground planes 80 through the thin dielectric portions 82 covering ground planes 80.

Figure 10:
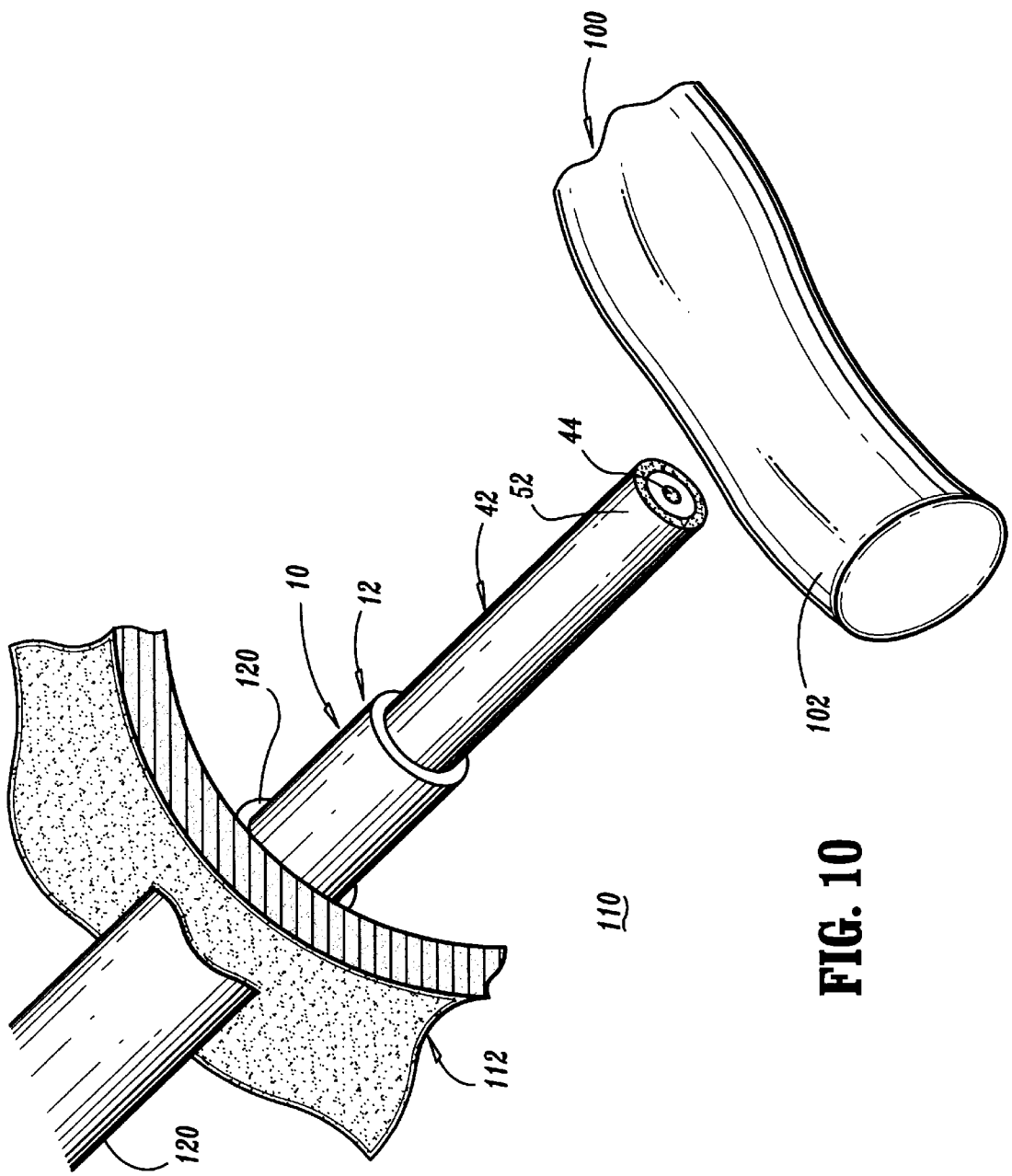
FIG. 10 is an enlarged perspective view of a vessel treated within an alternate embodiment of the microwave system.

In an alternate preferred embodiment, as illustrated in FIG. 10, instrument 12 is configured for surgical treatment of tissue relating to bodily joints and the like, such as arthroscopic applications. Chassis 18 includes outer tube 30 having microwave conductor 42 extending therethrough and axially movable therewithin, as described in greater detail hereinabove. In operation, as shown in FIG. 10, microwave conductor 42 is manipulated to advance distal end 52 in contact with tissue portion 104. Microwave energy is provided to instrument 12, as discussed previously. Due to the contact of distal end 52 of microwave conductor 42, microwave current flows from inner active conductor 44, through vessel portion 104, and through outer return conductor 46. Accordingly, tissue portion 104 becomes treated as desired.

It will be understood that various modifications may be made to the embodiments disclosed herein. For example, while specific preferred embodiments of the microwave system have been described in detail, structures that perform substantially the same function in substantially the same way to achieve the same result may also be used. In addition, the inner active and outer return conductors may include electrodes in a parallel configuration for treating tissue. Further, although an instrument having a chassis extension extending from the chassis is disclosed, it is contemplated that the chassis extension may extend from the microwave conductor. Moreover, the inner active and outer return conductors may include multiple electrode configurations. Therefore, the above description should not be construed as limiting, but merely as exemplifications of preferred embodiments. Those skilled in the art will envision other modifications within the scope and spirit of the claims appended hereto.

What is claimed is:

1. A method of closing a lumen of a body vessel, comprising the steps of:
   providing a surgical instrument having a tissue capturing portion and a microwave emitting portion, the tissue capturing portion being movable in relation to the microwave emitting portion;
   moving the microwave emitting portion of the surgical instrument in relation to the tissue capturing portion to capture a portion of the vessel therebetween and collapse the vessel lumen; and
   supplying microwave energy having a frequency ranging from about 400 MHZ to about 2500 MHZ to the microwave emitting portion of the surgical instrument to cause desiccation of vessel tissue to thereby substantially seal the vessel lumen in the collapsed position.

2. The method according to claim 1, wherein the microwave emitting portion of the surgical instrument includes a microwave conductor, and wherein the step of moving includes advancing the microwave conductor into direct contact with the portion of the vessel to be sealed.

3. The method according to claim 2, wherein the surgical instrument includes an elongated member the tissue capturing portion being supported at a distal end thereof, and wherein the step of moving includes positioning the surgical instrument such that the portion of the vessel to be sealed is disposed between the microwave conductor and the tissue capturing portion.

4. The method according to claim 3, wherein the step of moving includes clamping the portion of the vessel to be sealed between the microwave conductor and the tissue capturing portion.

5. The method according to claim 4, wherein the microwave conductor includes an active conductor and a return conductor mounted in coaxial arrangement, a forward conductor end of the microwave conductor being uninsulated to expose the active conductor and the return conductor, and wherein the step of moving includes directly contacting the portion of the vessel to be sealed with the forward conductor end.

6. An apparatus for application of microwave energy for sealing body tissue which comprises:
   an elongated member having proximal and distal ends, and defining a longitudinal axis, the elongated member having a tissue capturing portion supported on a distal end thereof;
   a microwave conductor being movably supported in relation to the elongated member and having an active conductor, a return conductor and a forward conductor end, the active conductor and the return conductor being mounted in a coaxial arrangement at the forward conductor end and the forward conductor end being positioned to engage the body tissue, the microwave conductor being supported by the elongated member to permit reciprocal axial movement relative to the tissue capturing portion of the elongated member between an unadvanced position wherein the forward conductor end is spaced proximally from the tissue capturing portion and an advanced position wherein the forward conductor end is adjacent the tissue capturing portion to engage and compress a portion of the body tissue captured between the microwave conductor and the tissue capturing portion; and
   a source of microwave energy in electrical contact with the microwave conductor for supplying microwave energy having a frequency ranging from about 400 MHZ to about 2500 MHZ to the microwave conductor.

7. The apparatus according to claim 6, wherein the forward conductor end of the microwave conductor is uninsulated to expose the active conductor and the return conductor to permit direct contact with the body tissue.

8. The apparatus according to claim 7, wherein the tissue capturing portion defines a tissue capturing surface, the tissue capturing surface comprising a dielectric material.

9. The apparatus according to claim 7, wherein the active conductor of the microwave conductor is dimensioned to extend distally beyond the return conductor.

10. The apparatus according to claim 7, including an insulating material disposed about a portion of the active conductor extending distally beyond the return conductor.

11. The apparatus according to claim 7, wherein the microwave conductor includes at least one ground plane in electrical contact with the return conductor.

12. The apparatus according to claim 11, including an insulating material disposed on a tissue contacting surface of the one ground plane.

13. The apparatus according to claim 7, wherein the return conductor of the microwave conductor is dimensioned to extend distally beyond the active conductor.

14. The apparatus according to claim 7, including a handle connected to the elongated member, the handle including a manual actuator operatively connected to the microwave conductor, the actuator being movable to effect movement of the microwave conductor between the unadvanced and the advanced positions.

15. The apparatus according to claim 6, further including an insulator mounted to the forward conductor end of the microwave conductor, the insulator preventing direct contact between the forward conductor end and the body tissue.

16. The apparatus according to claim 6, wherein at least a portion of the apparatus is constructed from a flexible material facilitating positioning capabilities of the apparatus in various orientations.

17. The apparatus according to claim 6, wherein at least a portion of the apparatus is constructed from a deformable material facilitating positioning capabilities of the apparatus in various orientations.

18. A method for sealing fibrous connective body tissue, comprising the steps of:
   providing a surgical instrument having a microwave emitting portion and a tissue capturing portion, the microwave emitting portion being advanceable in relation to the tissue capturing portion to compress fibrous connective body tissue therebetween;
   advancing the microwave emitting portion of the surgical instrument towards the tissue capturing portion of the surgical instrument to compress fibrous connective body tissue therebetween; and
   supplying microwave energy having a frequency ranging from about 400 MHZ to about 2500 MHZ to the microwave emitting portion of the surgical instrument to irradiate and cause a reduction in thickness of a portion of the fibrous connective body tissue the fibrous connective body tissue being irradiated to a temperature greater than or equal to about 65° C.

19. The method according to claim 18, wherein the step of supplying is continued to effect a reduction in thickness of the portion of the body tissue of about 25%–50%.

* * * * *